United States Patent [19]
Lake et al.

[11] Patent Number: 5,520,183
[45] Date of Patent: May 28, 1996

[54] FAT DEPTH MEASURING APPARATUS

[75] Inventors: Royden J. W. Lake; Ronald C. Bradbury, both of Armidale; Rainer Kunnemeyer, Mt. Warrigal, all of Australia

[73] Assignees: Meat Research Corporation, Sydney, Australia; University of New England, Armidale, Australia

[21] Appl. No.: 256,005

[22] PCT Filed: Dec. 21, 1992

[86] PCT No.: PCT/AU92/00675
§ 371 Date: Aug. 26, 1994
§ 102(e) Date: Aug. 26, 1994

[87] PCT Pub. No.: WO93/12419
PCT Pub. Date: Jun. 24, 1993

[30] Foreign Application Priority Data

Dec. 19, 1991 [AU] Australia .................. PL0107

[51] Int. Cl.$^6$ ................... A61B 8/00
[52] U.S. Cl. ................... 128/660.01
[58] Field of Search ............ 128/660.01, 660.06, 128/660.07; 73/602, 629

[56] References Cited

U.S. PATENT DOCUMENTS

| | | |
|---|---|---|
| 3,827,287 | 6/1974 | Boggs et al. . |
| 3,872,858 | 3/1975 | Hudson et al. . |
| 3,964,267 | 6/1976 | Jorgenson et al. . |
| 4,111,054 | 9/1978 | Jorgenson et al. . |
| 4,359,055 | 11/1982 | Carlson . |
| 4,359,056 | 11/1982 | Carlson . |
| 4,676,251 | 6/1987 | Bernatets ............... 128/660.06 |
| 4,785,817 | 11/1988 | Stouffer ............... 128/660.07 |

FOREIGN PATENT DOCUMENTS

B7327081 12/1983 Australia .
2432740 8/1978 France .
2643459 2/1989 France .
3915513 11/1990 Germany .

OTHER PUBLICATIONS

Comparison of Seven Ultrasound Techniques for In Vivo Estimation of Beef Carcass Composition (S. J. Parker et al) (1990).
The Use of Ultrasound to Predict the Carcass Composition of Live Cattle—A Review (G. Sim) (1983).
Operator and Machine Effects on Ultrasound Measurement of Beef Cows (D. R. C. Bailey et al) (1988).
Biomedical Ultrasonics (P. N. T. Wells, Academic Press, London) (1977).
Operating Manual for Model 1017A Backfat Meter (Dephi Industries Ltd, 1988).
Tennelec 1980's Catalogue.

*Primary Examiner*—George Manuel
*Attorney, Agent, or Firm*—Thomas M. Freiburger

[57] ABSTRACT

A fat depth measuring apparatus and method for use in measuring in an animal the depth of a fat layer between hide and muscle. An ultrasonic generator generates ultrasonic pulses and an ultrasonic echo detector generates echo signals indicative of ultrasonic pulses received by the detector after reflection from boundaries or discontinuities within the tissues of the animal. Variable gain amplifier amplifies the echo signals and produces detector signals. Gain control means varies the gain of the amplifier to increase the probability of having exactly two detector signals identifiable as arising from echoes from a hide/fat boundary and a fat/muscle boundary. A fat depth determining means receives the detector signals and if they exceed primary threshold levels identifies the two required detector signals so as to thereby enable determination of the depth of the fat layer. If more than three detector signals have levels exceeding 60% of the threshold level, the depth determination is considered invalid.

18 Claims, 3 Drawing Sheets

FAT DEPTH MEASURING APPARATUS

This invention relates to apparatus and a method to measure subcutaneous fat depth, e.g. on live cattle.

The measurement of subcutaneous fat depth is important for the efficient management of beef cattle production. It is an indicator of the proportion of the animal's weight which is saleable meat. Also, the fat content of the meat is an important factor to the consumer and subcutaneous fat depth is an indictor of the fat content of meat cuts. Ultrasound gives the opportunity of measuring fat depth on individual animals quickly, non-invasively, causing no harm to the animal and no change to the animal products. However throughout this specification reference to an "animal" includes the carcass of a slaughtered animal.

Two-dimensional ultrasound imaging (so-called 'B-mode imaging') has been used for measuring both fat depth and rib-eye muscle area. B-mode imaging requires considerable skill in the human operator to identify the structures that appear in the ultrasound image, especially the hide-fat interface and the fat-muscle interface which may be confused with interfaces within the hide, fat and muscle. Automating the process would make the equipment easier to use. Also, B-mode imaging equipment involves processing electronics and a special ultrasound transducer (consisting of either a mechanical scanned transducer element or an array of electronically scanned transducer elements) which allows the ultrasound beam to scan over the area of interest. Such equipment is expensive, too large to be hand-held and usually mains-powered.

It is an object of the meant invention to provide a fat depth measuring apparatus and method which is relatively simple and effective in use.

It is a preferred object to provide fat depth measuring apparatus which can be relatively small and cheaper than a B-mode imager, and which requires a minimum of skill to operate.

According to the present invention there is provided a fat depth measuring apparatus for use in measuring in an animal the depth of a fat layer between hide and muscle, the apparatus including an ultrasonic generator for generating ultrasonic pulses and for transmitting the ultrasonic pulses into the animal through the hide towards the subcutaneous fat and muscle tissues an ultrasonic echo detector operative to generate echo signals indicative of ultrasonic pulses received by the detector after reflection from boundaries or discontinuities within the tissues of the animal, the apparatus being characterised by a variable gain amplifier operative to amplify the echo signals and to produce detector signals, gain control means operative to vary the gain of the amplifier to increase the probability of having two detector signals identifiable as arising from echoes of the ultrasonic pulses from a hide/fat boundary and a fat/muscle boundary of the animal, and a fat depth determining means receiving the detector signals and operative to identify the two required detector signals indicative of ultrasonic echo pulses arising from reflection from the hide/fat boundary and fat/muscle boundary respectively so as to thereby enable determination of the depth of the fat layer.

Preferably the fat depth determining means is operative to identify the required detector signals by testing whether the magnitude of the detector signals produced by reflected ultrasonic pulses exceed respective primary threshold levels. The apparatus preferably includes time gain compensation means for increasing the gain of the amplifier during the period of time following generation of each ultrasonic pulse whereby ultrasonic echo pulses reflected from deeper within the tissues of the animal are amplified by a progressively increasing amplification level, the two required detector signals identifiable as being caused by reflections from the hide/fat boundary and fat/muscle boundary respectively both exceeding a common primary threshold level before being identified as the required detector signals.

The fat depth determining means includes a threshold detector circuit for determining if detector signals exceed the primary threshold levels, the threshold detector circuit being rendered insensitive for a short time period commencing when the threshold detector circuit identifies a detector signal exceeding the respective primary threshold level.

The fat depth determining means includes a lower threshold detection means operative to determine if the two required detector signals are the only detector signals exceeding in magnitude a lower threshold level which is lower than the primary threshold levels required for identification of the required detector signals, the fat depth determining means being operative to invalidate the fat depth determining operation if three or more detector signals including the two required detector signals exceed the lower threshold level. This helps to ensure that fat depth determinations are not made if there are three or more strong echo signals leading to possible uncertainty or ambiguity in identifying the two echo signals from the hide/fat and fat/muscle boundaries. In this embodiment, the lower threshold level may comprise a detector signal magnitude equal to about sixty per cent of the magnitude of the primary threshold levels.

The fat depth determining means preferably includes an interval timer operative to determine the time interval between the two required detector signals, that time interval providing a measure of the depth of the fat layer between the hide/fat and fat/muscle boundaries.

The gain control means preferably includes a gain magnitude control means, the fat depth determining means including dual signal detecting means operative to determine if two identifiable detector signals have been generated following generation of an ultrasonic pulse, the gain magnitude control means being responsive to the dual signal detector means to increase the magnitude of the gain of the amplifier if less than two identifiable detector signals have been generated and to decrease the magnitude of the gain of the amplifier if more than two identifiable detector signals have been generated. By means of this gain magnitude control responsive to a dual signal detector means, the apparatus can be automatically adjusted so that two and only two detector signals are identified and used for determination of the fat thickness.

An input protection gating circuit may be operative during generation of the ultrasonic pulses by the ultrasonic generator to stop generation of the detector signals, therby reducing interfering signals during the pulse generation.

A window timer may be provided for controlling a hide/fat interface timing window commencing a predetermined time after generation of the ultrasonic pulse, the hide/fat interface timing window covering the period of time when an ultrasonic pulse echo from the hide/fat boundary is expected, the fat depth determining means being operative only if the first of the two required detector signals is generated within the hide/fat interface timing window. This also helps to accurately discriminate the first required detector signal.

The gain control means may include a time gain compensation means operative, during a period of time following generation of each ultrasonic pulse when existence of the two required detector signals is being sought, to progressively increase the magnitude of the gain of the amplifier. This compensates for the weaker echo signals from deeper tissues.

The time gain compensation means may be operative at a predetermined time interval after the time of generation of the ultrasonic pulse to rapidly increase the magnitude of the gain of the amplifier and thereafter to more slowly progressively increase the magnitude of the gain of the amplifier, the predetermined time interval corresponding to the minimum anticipated transmission time for an ultrasonic pulse passing through the hide of the animal and being reflected from the hide/fat boundary in the case of a hide having a minimum anticipated thickness. The time gain compensation means is preferably operative to increase the magnitude of the gain of the amplifier at an exponential rate, since the strength of echo pulses from deeper tissues reduces exponentially.

Preferably the fat depth determining means is operative only if the two required detector signals occur before expiry of a maximum time interval running from the time of generation of the ultrasonic pulse, the duration of the maximum time interval being chosen to reduce the likelihood of a reflection from a deeper tissue boundary such as a muscle/bone boundary being detected and identified as the second of the two required detector signals.

A detector signal quality indicator may be operative to provide an indication of the number or proportion of the ultrasonic pulses being generated which lead to exactly two identifiable detector signals being generated. By providing such a detector signal quality indicator, the operator of the apparatus can monitor the placement and operation of the apparatus so that a relatively high proportion or number of the ultrasonic pulses are leading to fat depth measurements being made.

The present invention also provides a method for use in measuring in an animal the depth of a fat layer between hide and muscle, the method including the steps of generating ultrasonic pulses and transmitting the ultrasonic pulses into the animal through the hide towards the subcutaneous fat and muscle tissues, detecting ultrasonic echo pulses and generating echo signals indicative of ultrasonic echo pulses received after reflection from boundaries or discontinuities within the tissues of the animal, the method being characterised by the steps of amplifying the echo signals to produce detector signals, varying the level of the amplification to increase the probability of having two detector signals identifiable as arising from echoes of the ultrasonic pulses from a hide/fat boundary and a fat/muscle boundary of the animal, receiving the detector signals and identifying the two required detector signals indicative of ultrasonic echo pulses arising from reflections from the hide/fat boundary and fat/muscle boundary respectively so as to thereby enable determination of the depth of the fat layer.

The step of identifying the required detector signals preferably comprises testing whether the magnitude of the detector signals produced by reflected ultrasonic pulses exceed respective primary threshold levels. This step preferably also includes determining if the two required detector signals are the only detector signals exceeding in magnitude a lower threshold level which is lower than the primary threshold levels required for identification of the required detector signals, the fat depth determining operation being invalidated if three or more detector signals including the two required detector signals exceed said lower threshold level. The lower threshold level may comprise a detector signal magnitude equal to about sixty per cent of the magnitude of the primary threshold levels.

The method may further include a step of generating a hide/fat interface timing window commencing a predetermined time after generation of each ultrasonic pulse, the hide/fat interface timing window covering the period of time when an ultrasonic pulse echo from the hide/fat boundary is expected, the step of identifying the two required detector signals being performed only if the first of the two required detector signals is generated within the hide/fat interface timing window.

Preferably the step of identifying the two required detector signals is performed only if the two required detector signals occur before expiry of a maximum time interval running from the time of generation of the ultrasonic pulse, the duration of the maximum time interval being chosen to reduce the likelihood of a reflection from a deeper tissue boundary such as a muscle/bone boundary being detected and identified as the second of the two required detector signals.

The method may further include a step of providing an indication of the number or proportion of the ultrasonic pulses being generated which lead to exactly two identifiable detector signals being generated.

Possible and preferred features of the present invention will now be described with particular reference to the accompanying drawings. However it is to be understood that the features illustrated in and described with reference to the drawings are not to be construed as limiting on the scope of the invention. In the drawings.

Figure 1:
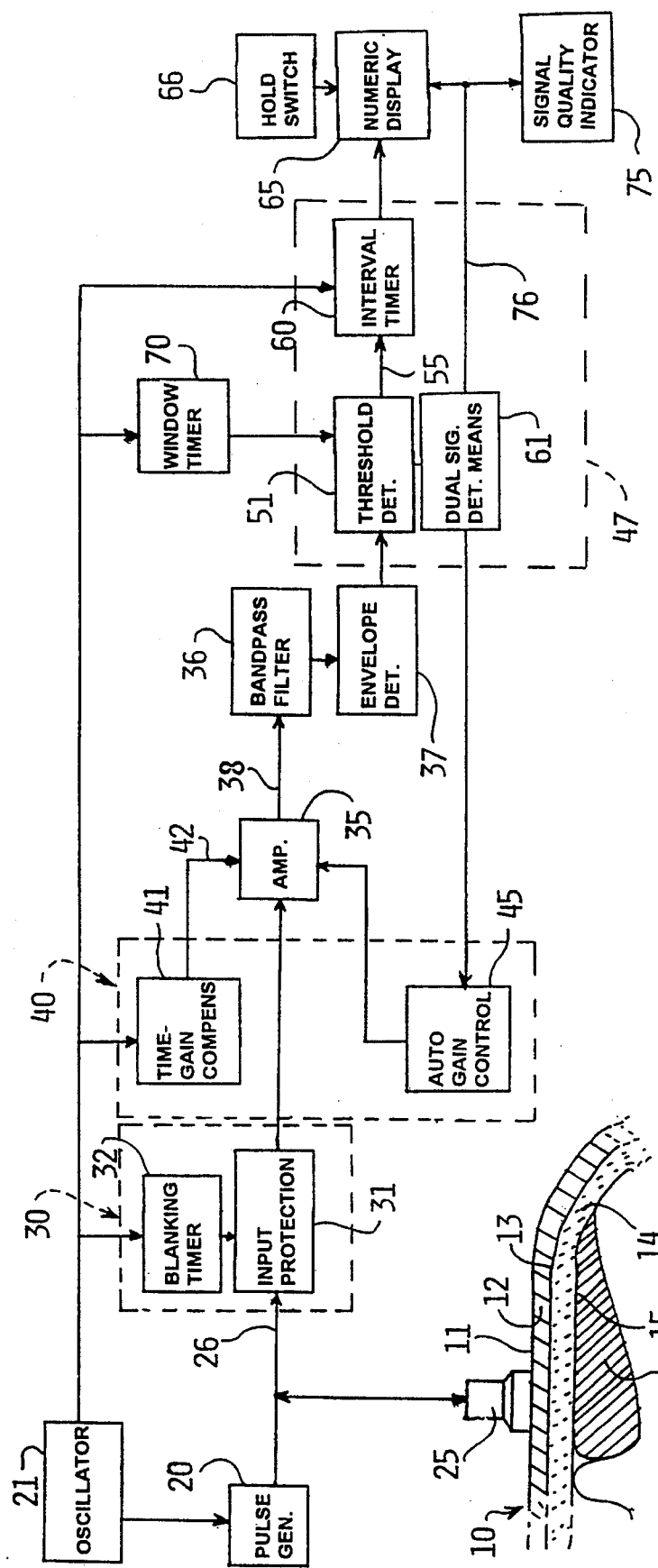
FIG. 1 is a block diagram of apparatus according to the present invention.
Figure 2:
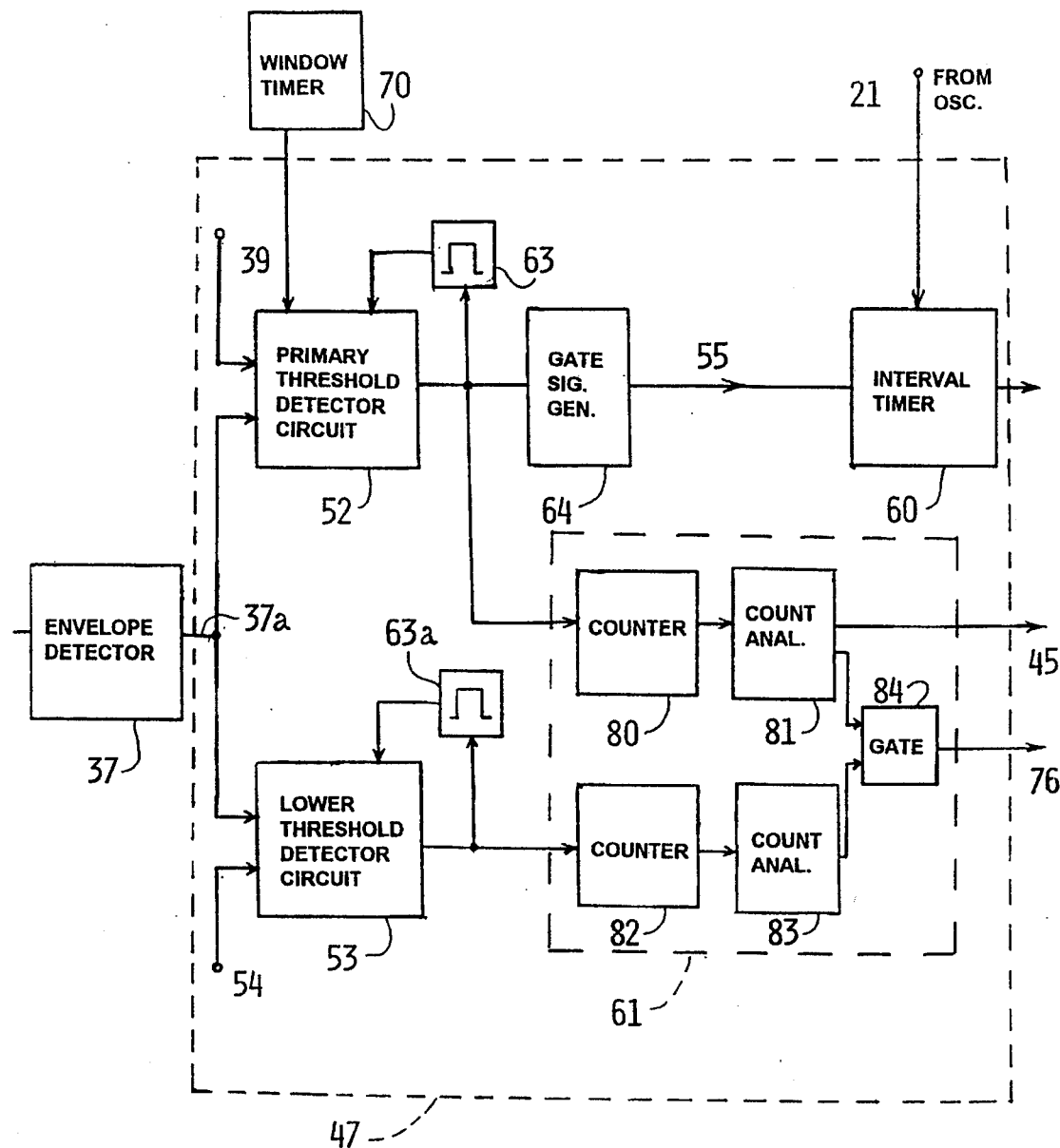
FIG. 2 is a schematic block diagram of a possible construction of the fat depth determining means.

The apparatus includes a pulse generator 20 supplied by oscillator 21 and producing a train of narrow, high voltage transmit pulses and at each pulse, the ultrasound transducer 25 emits a short ultrasound pulse. The operator places the ultrasound transducer 25 onto the surface 11 of the animal's hide 12 at the site of interest typically over the rib-eye muscle at the level of the 12th–13th rib or over the rump at the level of the pin bone. At these sites, between the hide 12 and muscle 16, there is a layer of subcutaneous fat 14 for which the thickness is indicative of the amount of fat in the animal 25. The ultrasound pulses propagate from the ultrasound transducer through the hide 12 and underlying tissue in a line approximately perpendicular to the surface 11 of the hide 12. Any point on this path where there is a change in acoustic impedance gives rise to a partial reflection. Part of this reflected wave travels back to the ultrasound transducer 25, now acting as a receiver, where a corresponding electrical voltage echo pulse 26 is generated.

Typically, a liquid such as cooking oil or water is used to provide ultrasonic coupling between the ultrasound transducer 25 and the hide surface 11. Once good coupling is achieved, the instrument can make a large number of independent measurements in a short time interval. The interval between measurements must be large enough that the ultrasound pulses from one transmit pulse have died away before the next transmit pulse and small enough for the automatic gain control loop to stabilise (as explained later) and update the display at a satisfactory rate for the operator; 2 msec. being typical. During this interval the electronics logic can make a number of decisions about the acceptability of each measurement.

It has been observed that the largest magnitude reflections occur at the hide/fat boundary 13 and the fat/muscle boundary 15. However, lower-amplitude reflections often occur within the hide layer 12 and within the muscle 16. Lower-amplitude reflections may also occur from layering within the fat layer 14. These lower amplitude reflections can easily be confused with the hide/fat or fat/muscle boundary reflections and special care is required in implementing circuitry to distinguish between the real and spurious boundaries. In the present preferred embodiment this is achieved by: (1) a particularly shaped time gain compensation which allows both the hide/fat and fat/muscle echoes to be within the detectable range; (2) the inclusion of automatic gain control which is adjusted up or down until two and only two echo pulses are detected in the window of valid depths; (3) the use of dual threshold detection by which it can be verified that all spurious echo signals are less than x% of the desired two echo signals, where x is typically 60; (4) the use of an echo signal indicator, so that the operator can judge the quality of the received echoes; and (5) the optional ability to automatically histogram a large number of independent measurements and interpret the actual fat depth from specific features of this histogram.

The fat depth (d) is simply related to the time (t) between the fat/muscle boundary echo and the hide/fat boundary echo, and the ultrasound propagation velocity in fat (v) thus:

$$d = vt/2$$

where the factor 2 allows for the ultrasound pulse travelling through the fat layer 14 twice.

The function of the overall apparatus is to measure the time between the two largest pulses occurring within the limits of the fat layer 14 and display this time appropriately scaled, as the fat depth. A further preferred function of the apparatus is to validate the fat depth measurement.

In the input protection gating circuit 30, the echo signal on line 26 is clipped in amplitude and blanked by input protection gate 31 under control of blanking timer 32 at, and immediately following, the transmit pulse from generator 20, e.g. for a period of 2.6 usec.

The echo signal 26 is then amplified by the variable gain amplifier 35. The gain adjustment means 40 for the amplifier 35 has two components: time-gain compensation means 41 and automatic gain control 45. Both of these components are automatically adjusted by the circuits with the automatic gain control 45 adjustment being dependent on the quality of the previous echo signal.

Time-gain compensation by means 41 involves changing the gain of amplifier 35 as each echo signal 26 is being received, following each transmit pulse at time t0. Initially the gain is held low. In combination with the input protection gating circuit 30, this prevents the large-amplitude transmit pulse from generator 20 generated at time t0 (see FIG. 37) from subsequently being detected. The gain of amplifier 35 is rapidly increased after time t1 (typically 3.6 usec. after t0) until the gain is sufficient to amplify the echo signals 26 to a usable level. The gain is then made to increase slowly to compensate for the progressive attenuation of any echo pulses with time (i.e. depth of tissues). This is achieved by generating a gain control ramp signal on line 42 by the time-gain compensation means 41 consisting of a fast rate of change at t1 followed by a slow rate of change. The combination of a linear gain control ramp on line 42 and an exponential gain-versus-control characteristic in the variable gain amplifier 35 gives an exponentially increasing gain with time. This compensates for the exponentially decreasing echo signal level with time due to progressive attenuation of the ultrasound pulse. The time-gain compensation provided by circuit 41 may be varied if necessary to suit different animal species. All gain changes are preferably done smoothly without the introduction of discontinuities such as stepped voltages as any sudden gain changes may introduce spurious pulses into the signal being analysed.

Figure 3:
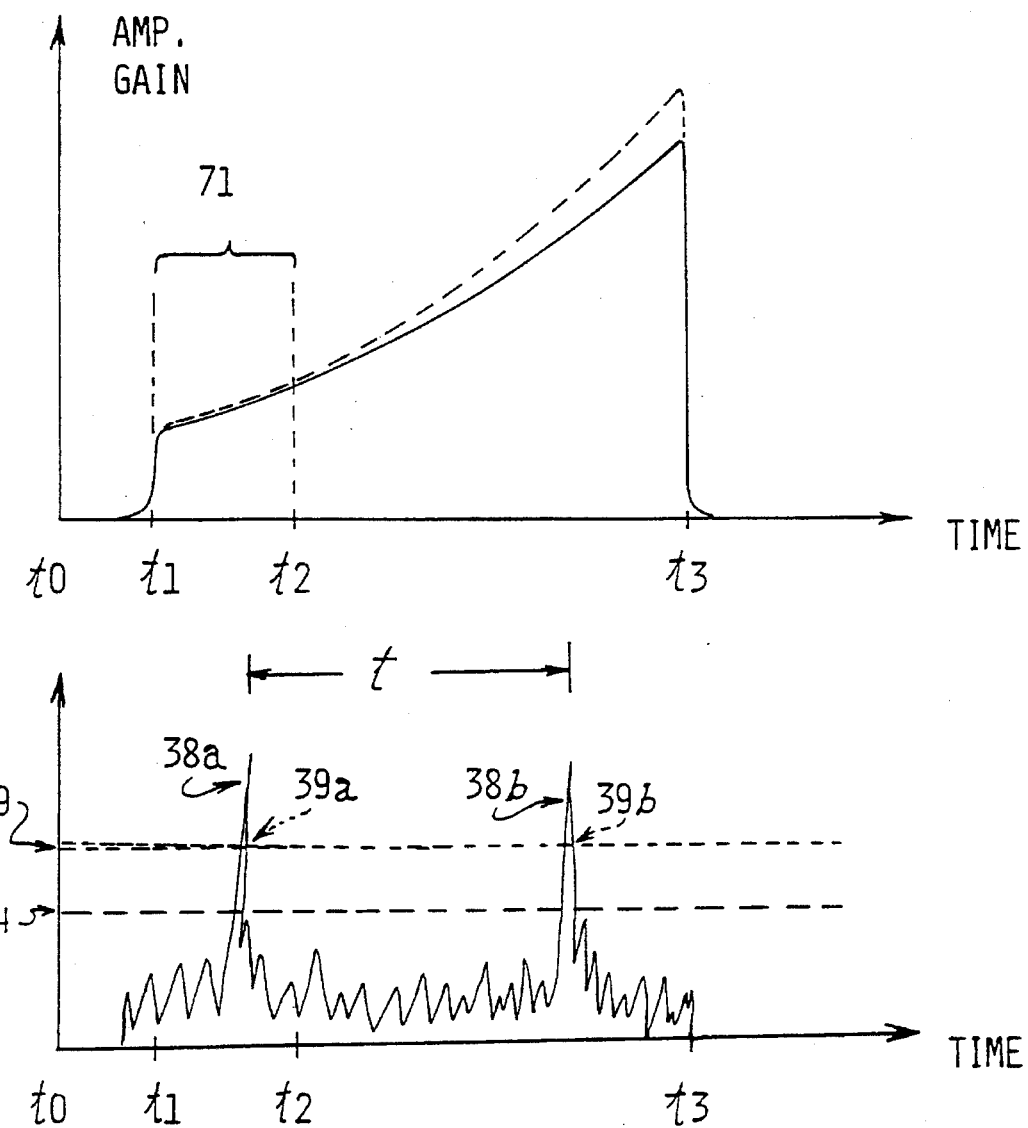
FIG. 3 illustrates possible signal waveforms to help explain operation of the preferred apparatus.

Automatic gain control means 45 changes the gain of amplifier 35 to compensate for variation in reflectivity at the hide/fat and fat/muscle boundaries 13, 15. The intention is to detect the largest two echo pulses. If exactly two pulses are detected, the gain is left constant for the next transmit pulse. If more than two pulses are detected the gain is decreased, otherwise it is increased as shown in broken line in FIG. 3. Over a number of transmit pulse sequences the gain will automatically adjust to the required level.

The output of the variable gain amplifier 35 is passed through a bandpass filter 36 to reduce the out-of-band noise. The centre-frequency of the filter 36 is matched to the centre-frequency of the ultrasound transducer 25. The output is rectified and low-pass filtered in envelope circuit 37 to obtain the envelope which is fed to a fat depth determining means 47 which includes a threshold detector 51 including detector circuit 52. If the envelope signal 37a from circuit 37 exceeds the reference threshold 39, the detector 52 generates an output pulse on line 55. Both hysteresis and debouncing may be used in the threshold detector 51 to ensure a single pulse is output on line 55 for each echo. Debouncing involves generating by means 63 a time period, starting at the time when the detector circuit 52 generates the pulse leading edge, during which the detector circuit 52 is insensitive to its input 37a from envelope detector 37. In this way, short term oscillations and electrical noise superimposed on the echo signal will not cause multiple pulses on line 55 being output by the detector circuit 52. Furthermore, hysteresis can ensure the detector circuit 52 is free from oscillation itself. A gate signal generated by gate signal generator 64 on line 55 switches high at the first pulse (corresponding to the superficial surface 13 of the fat) and starts the interval timer 60 counting clock pulses from oscillator 21 then, at the second pulse (the deep surface 15 of the fat), the gate signal 55 switches low stopping the count in the interval timer 60.

The clock pulse interval may be chosen to correspond to the time taken for the ultrasound echo to travel a depth of 0.1 mm at the known ultrasound propagation velocity in fat. In this way the count in the 3-digit BCD interval counter 60 gives the fat-depth directly in 0.1 mm units so the count may be directly displayed on a 3-digit readout in the display 65. For an ultrasound propagation velocity of 1,470 meters/sec a clock pulse frequency of 7.35 MHz is used. Alternatively, the display 65 can be calibrated to read the same as B-mode ultrasound imaging machines. The distance measurement in these machines is normally calibrated for 1.540 meters/sec in which case a clock pulse frequency of 7.70 MHz is needed.

Additional criteria are desirable although not essential to optimise the probability that the fat depth measurement is valid. These involve a hide/fat boundary window, a second threshold detector and a depth window.

A hide/fat interface timing window 71 (FIG. 3) between times t1 and t2 may be generated by window timer 70 to cover the period of time when the hide/fat boundary echo is expected. Cattle hide thickness generally lies in the range 3 to 9 mm. An echo pulse must be detected by detector 51 within this window 71 for a valid measurement.

The two detector circuits 52, 53 in the detector 51 have the same input signal but have different thresholds 39, 54. Typically the lower detector threshold level 54 is 60% of the higher threshold 39. The lower threshold detector circuit 53 includes means 63a to achieve a debouncing function, similar to means 63 of detector circuit 52. The number of pulses detected by the detector 51 must be exactly two for a valid reading. To pass this criterion, the echo signal 26 when amplified to form the detector signal 38 and passed through filter 36 and envelope detector 37 to form envelope signal 37a must have two distinct peaks with any other peaks caused by echoes, such as might arise from layering within the fat, being at most 60% of the main pulses 38a, 38b in amplitude. If the amplitude of the interfering pulses approaches the amplitude of the main pulses 38a, 38b, then there may be doubt as to which pulses are the correct pulses to time. The dual signal detector means 61 counts and analyses the outputs of the detector circuits 52, 53. Counter 80 and count analyser 81 determine if the primary threshold detector circuit 52 detects more or less than two signals exceeding the threshold 39 and generates an appropriate output to control the automatic gain control means 45. The counter 82 and count analyser 83 determine if more than three pulses exceed the lower threshold level 54. Gate 84 determines from the count analysers 81 and 83 if exactly two pulses exceed the primary threshold 39 and not more than two pulses exceed the lower threshold 54 and, if so, a valid signal output on line 76 is generated. Therefore, when three or more pulses are detected by the lower threshold detector circuit 53, the measurement will not be accepted as valid.

The time t for a pulse to traverse the fat layer 14 twice is measured by counting in interval time 60 clock pulses from the time the higher threshold detector 52 is first set high to the time that it is set high for a second time.

A depth window may be timed by timer 70 from the end at time t1 of the input blanking interval for a fixed period ending at time t3 corresponding to the greatest depth of interest (typically 60 usec.). Pulses occurring after the end of the depth window at time t3, which might arise from bone reflections, are ignored.

If an individual measurement passes the criteria then the fat depth is displayed by numerical display 65, otherwise the display digits are blanked by the signal on line 76. To allow the operator time to read the number being displayed, the displayed value is held for approximately 300 msec. A display hold push-button switch 66 may also be provided.

A signal quality indicator 75 consisting of a 3-segment (4-state) bar graph is included on the apparatus display to give feedback to help the operator in placing the transducer 25. The valid signal on line 76 is low-pass filtered and input to 3 comparators, each of which drives a segment of a bar graph. If no valid measurements are being made, the valid signal will be constantly low and all segments of the bar graph will be off. If the operator adjusts the transducer 25 such that progressively more of the measurements are valid, the filtered valid signal indicated by display 75 will increase, activating 1, 2 and then 3 segments of the bar graph.

Optionally, a microprocessor, programmable logic device or programmable logic array (not shown) may be included to carry out some of the described functions and to provide additional facilities to the fat depth meter. Described and illustrated circuit functions that can be performed or controlled by microprocessor include the oscillator 21, blanking timer 32, gain control means 40, window timer 70, fat depth determining means 47 including elements 60, 64, 80–84, display 65, and signal quality indicator 75. The microprocessor may perform the following additional functions:

read in measurement data from the circuit, calculate average values of fat depth, calculate and display histograms of measurement data, detect and reject outlying measurement values, adjust settings in the circuit, log measurements for later analysis, telemeter data to a computer or data logging device, perform self-testing, calibration and fault-analysis.

The fat depth determining method provided by the invention comprises the steps or operations carried out by the apparatus, and the prefered steps will be readily understood from the preceding description of the prefered embodiment of the apparatus.

It will be seen that the fat depth measuring apparatus as herein described and illustrated can be simple to use, can be accurate and provide indication of the probability that the fat depth determination is accurate. The apparatus can be compact, battery powered and relatively inexpensive.

We claim:

1. A fat depth measuring apparatus for use in measuring in an animal the depth of a fat layer between hide and muscle, the apparatus including an ultrasonic generator for generating ultrasonic pulses and for transmitting the ultrasonic pulses into the animal through the hide towards the subcutaneous fat and muscle tissues, an ultrasonic echo detector operative to generate echo signals indicative of ultrasonic pulses received by the detector after reflection from boundaries or discontinuities within the tissues of the animal, the apparatus being characterised by a variable gain amplifier operative to amplify the echo signals and to produce detector signals, gain control means operative to vary the gain of the amplifier to increase the probability of having two detector signals identifiable as arising from echoes of the ultrasonic pulses from a hide/fat boundary and a fat/muscle boundary of the animal, and a fat depth determining means receiving the detector signals and operative to identify the two required detector signals indicative of ultrasonic echo pulses arising from reflection from the hide/fat boundary and fat/muscle boundary respectively, the fat depth determining means being operative to identify the required detector signals by testing whether the magnitude of the detector signals produced by reflected ultrasonic pulses exceed respective primary threshold levels, so as to thereby enable determination of the depth of the fat layer.

2. Apparatus as claimed in claim 1 characterised in that the gain control means includes a time gain compensation means operative, during a period of time following generation of each ultrasonic pulse when existence of the two required detector signals is being sought, to progressively increase the magnitude of the gain of the amplifier.

3. Apparatus as claimed in claim 2 characterised in that the time gain compensation means is operative at a predetermined time interval after the time of generation of the ultrasonic pulse to rapidly increase the magnitude of the gain of the amplifier and thereafter to more slowly progressively increase the magnitude of the gain of the amplifier, the predetermined time interval corresponding to the minimum anticipated transmission time for an ultrasonic pulse passing through the hide of the animal and being reflected from the hide/fat boundary in the case of a hide having a minimum anticipated thickness.

4. Apparatus as claimed in claim 2 characterised in that the time gain compensation means is operative to increase the magnitude of the gain of the amplifier at an exponential rate.

5. A fat depth measuring apparatus for use in measuring in an animal the depth of a fat layer between hide and muscle, the apparatus including an ultrasonic generator for generating ultrasonic pulses and for transmitting the ultrasonic pulses into the animal through the hide towards the subcutaneous fat and muscle tissues, an ultrasonic echo detector operative to generate echo signals indicative of ultrasonic pulses received by the detector after reflection from boundaries or discontinuities within the tissues of the animal, a variable gain amplifier operative to amplify the echo signals and to produce detector signals, gain control means operative to vary the gain of the amplifier to increase the probability of having two detector signals identifiable as arising from echoes of the ultrasonic pulses from a hide/fat boundary and a fat/muscle boundary of the animal, and a fat depth determining means receiving the detector signals and operative to identify the two required detector signals indicative of ultrasonic echo pulses arising from reflection from the hide/fat boundary and fat/muscle boundary respectively so as to thereby enable determination of the depth of the fat layer, the fat depth determining means being operative to identify the required detector signals by testing whether the magnitude of the detector signals produced by reflected ultrasonic pulses exceed respective primary threshold levels, the fat depth determining means including a lower threshold detection means operative to determine if said two required detector signals are the only detector signals exceeding in magnitude a lower threshold level which is lower than said primary threshold levels, said fat depth determining means being operative to invalidate the fat depth determining operation if three or more detector signals including said two required detector signals exceed said lower threshold level.

6. Apparatus as claimed in claim 5 and further characterised by time gain compensation means for increasing the gain of the amplifier during the period of time following generation of each ultrasonic pulse whereby ultrasonic echo pulses reflected from deeper within the tissues of the animal are amplified by a progressively increasing amplification level, the two required detector signals identifiable as being caused by reflections from the hide/fat boundary and fat/muscle boundary respectively both exceeding a common primary threshold level before being identified as the required detector signals.

7. Apparatus as claimed in claim 5 characterised in that the fat depth determining means includes a threshold detector circuit for determining if detector signals exceed the primary threshold levels, the threshold detector circuit being rendered insensitive for a short time period commencing when the threshold detector circuit identifies a detector signal exceeding the respective primary threshold level.

8. Apparatus as claimed in claim 5 characterised in that said lower threshold level comprises a detector signal magnitude equal to about sixty per cent of the magnitude of said primary threshold levels.

9. A fat depth measuring apparatus for use in measuring in an animal the depth of a fat layer between hide and muscle, the apparatus including an ultrasonic generator for generating ultrasonic pulses and for transmitting the ultrasonic pulses into the animal through the hide towards the subcutaneous fat and muscle tissues, an ultrasonic echo detector operative to generate echo signals indicative of ultrasonic pulses received by the detector after reflection from boundaries or discontinuities within the tissues of the animal, a variable gain amplifier operative to amplify the echo signals and to produce detector signals, gain control means operative to vary the gain of the amplifier to increase the probability of having two detector signals identifiable as arising from echoes of the ultrasonic pulses from a hide/fat boundary and a fat/muscle boundary of the animal, and a fat depth determining means receiving the detector signals and operative to identify the two required detector signals indicative of ultrasonic echo pulses arising from reflection from the hide/fat boundary and fat/muscle boundary respectively so as to thereby enable determination of the depth of the fat layer, the fat depth determining means including an interval timer operative to determine the time interval between the two required detector signals, that time interval providing a measure of the depth of the fat layer between the hide/fat and fat/muscle boundaries.

10. A fat depth measuring apparatus for use in measuring in an animal the depth of a fat layer between hide and muscle, the apparatus including an ultrasonic generator for generating ultrasonic pulses and for transmitting the ultrasonic pulses into the animal through the hide towards the subcutaneous fat and muscle tissues, an ultrasonic echo detector operative to generate echo signals indicative of ultrasonic pulses received by the detector after reflection from boundaries or discontinuities within the tissues of the animal, a variable gain amplifier operative to amplify the echo signals and to produce detector signals, gain control means operative to vary the gain of the amplifier to increase the probability of having two detector signals identifiable as arising from echoes of the ultrasonic pulses from a hide/fat boundary and a fat/muscle boundary of the animal, the gain control means including a gain magnitude control means, the fat depth determining means including dual signal detecting means operative to determine if two identifiable detector signals have been generated following generation of an ultrasonic pulse, the gain magnitude control means being responsive to the dual signal detector means to increase the magnitude of the gain of the amplifier if less than two identifiable detector signals have been generated and to decrease the magnitude of the gain of the amplifier if more than two identifiable detector signals have been generated, and a fat depth determining means receiving the detector signals and operative to identify the two required detector signals indicative of ultrasonic echo pulses arising from reflection from the hide/fat boundary and fat/muscle boundary respectively so as to thereby enable determination of the depth of the fat layer.

11. A fat depth measuring apparatus for use in measuring in an animal the depth of a fat layer between hide and muscle, the apparatus including an ultrasonic generator for generating ultrasonic pulses and for transmitting the ultrasonic pulses into the animal through the hide towards the subcutaneous fat and muscle tissues, an ultrasonic echo detector operative to generate echo signals indicative of ultrasonic pulses received by the detector after reflection from boundaries or discontinuities within the tissues of the animal, a variable gain amplifier operative to amplify the echo signals and to produce detector signals, gain control means operative to vary the gain of the amplifier to increase the probability of having two detector signals identifiable as arising from echoes of the ultrasonic pulses from a hide/fat boundary and a fat/muscle boundary of the animal, a fat depth determining means receiving the detector signals and operative to identify the two required detector signals indicative of ultrasonic echo pulses arising from reflection from the hide/fat boundary and fat/muscle boundary respectively so as to thereby enable determination of the depth of the fat layer, and a window timer for controlling a hide/fat interface timing window commencing a predetermined time after generation of the ultrasonic pulse, the hide/fat interface timing window covering the period of time when an ultrasonic pulse echo from the hide/fat boundary is expected, the fat depth determining means being operative only if the first of the two required detector signals is generated within the hide/fat interface timing window.

12. A fat depth measuring apparatus for use in measuring in an animal the depth of a fat layer between hide and muscle, the apparatus including an ultrasonic generator for generating ultrasonic pulses and for transmitting the ultrasonic pulses into the animal through the hide towards the subcutaneous fat and muscle tissues, an ultrasonic echo detector operative to generate echo signals indicative of ultrasonic pulses received by the detector after reflection from boundaries or discontinuities within the tissues of the animal, a variable gain amplifier operative to amplify the echo signals and to produce detector signals, gain control means operative to vary the gain of the amplifier to increase the probability of having two detector signals identifiable as arising from echoes of the ultrasonic pulses from a hide/fat boundary and a fat/muscle boundary of the animal, and a fat depth determining means receiving the detector signals and operative to identify the two required detector signals indicative of ultrasonic echo pulses arising from reflection from the hide/fat boundary and fat/muscle boundary respectively so as to thereby enable determination of the depth of the fat layer, the fat depth determining means being operative only if the two required detector signals occur before expiry of a maximum time interval running from the time of generation of the ultrasonic pulse, the duration of the maximum time interval being chosen to reduce the likelihood of a reflection from a deeper tissue boundary such as a muscle/bone boundary being detected and identified as the second of the two required detector signals.

13. A fat depth measuring apparatus for use in measuring in an animal the depth of a fat layer between hide and muscle, the apparatus including an ultrasonic generator for generating ultrasonic pulses and for transmitting the ultrasonic pulses into the animal through the hide towards the subcutaneous fat and muscle tissues, an ultrasonic echo detector operative to generate echo signals indicative of ultrasonic pulses received by the detector after reflection from boundaries or discontinuities within the tissues of the animal, a variable gain amplifier operative to amplify the echo signals and to produce detector signals, gain control means operative to vary the gain of the amplifier to increase the probability of having two detector signals identifiable as arising from echoes of the ultrasonic pulses from a hide/fat boundary and a fat/muscle boundary of the animal, and a fat depth determining means receiving the detector signals and operative to identify the two required detector signals indicative of ultrasonic echo pulses arising from reflection from the hide/fat boundary and fat/muscle boundary respectively so as to thereby enable determination of the depth of the fat layer, a detector signal quality indicator operative to provide an indication of the number or proportion of the ultrasonic pulses being generated which lead to exactly two identifiable detector signals being generated.

14. A method for use in measuring in an animal the depth of a fat layer between hide and muscle, the method including the steps of generating ultrasonic pulses and transmitting the ultrasonic pulses into the animal through the hide towards the subcutaneous fat and muscle tissues, detecting ultrasonic echo pulses and generating echo signals indicative of ultrasonic echo pulses received after reflection from boundaries or discontinuities within the tissues of the animal, the method being characterized by the steps of amplifying the echo signals to produce detector signals, varying the level of amplification to increase the probability of having two detector signals identifiable as arising from echoes of the ultrasonic pulses from a hide/fat boundary and a fat/muscle boundary of the animal, receiving the detector signals and identifying the two required detector signals indicative of ultrasonic echo pulses arising from reflections from the hide/fat boundary and fat/muscle boundary respectively so as to thereby enable determination of the depth of the fat layer, the step of identifying the required detector signals comprising testing whether the magnitude of the detector signals produced by reflected ultrasonic pulses exceed respective primary threshold levels, the fat depth determining operation being invalidated if three or more detector signals including said two required detector signals exceed said lower threshold level.

15. A method as claimed in claim 14 characterised in that said lower threshold level comprises a detector signal magnitude equal to about sixty per cent of the magnitude of said primary threshold levels.

16. A method as claimed in claim 14 and further characterised by a step of generating a hide/fat interface timing window commencing a predetermined time after generation of each ultrasonic pulse, the hide/fat interface timing window covering the period of time when an ultrasonic pulse echo from the hide/fat boundary is expected, the step of identifying the two required detector signals being performed only if the first of the two required detector signals is generated within the hide/fat interface timing window.

17. A method as claimed in claim 14 characterised in that the step of identifying the two required detector signals is performed only if the two required detector signals occur before expiry of a maximum time interval from the time of generation of the ultrasonic pulse, the duration of the maximum time interval being chosen to reduce the likelihood of a reflection from a deeper tissue boundary such as a muscle/bone boundary being detected and identified as the second of the two required detector signals.

18. A method as claimed in claim 14 and further characterised by a step of providing an indication of the number or proportion of the ultrasonic pulses being generated which lead to exactly two identifiable detector signals being generated.

* * * * *